United States Patent [19]

Le Gigan

[11] Patent Number: 5,253,512
[45] Date of Patent: Oct. 19, 1993

[54] MOISTURE METER FOR GRANULAR OR POWDERED PRODUCTS, AND METHOD FOR MEASURING THE DEGREE OF MOISTURE

[75] Inventor: Dominique Le Gigan, Parmain, France

[73] Assignee: Star Partners, Chicago, Ill.

[21] Appl. No.: 897,271

[22] Filed: Jun. 11, 1992

[30] Foreign Application Priority Data

Jun. 13, 1991 [FR] France .................... 9107215

[51] Int. Cl.⁵ .................... G01N 19/10; G01N 27/22; G01N 21/85
[52] U.S. Cl. ........................ 73/73; 374/142; 374/143
[58] Field of Search ............... 73/73; 374/142, 143

[56] References Cited

U.S. PATENT DOCUMENTS

| | | |
|---|---|---|
| 2,834,201 | 5/1958 | Ohlheiser . |
| 3,840,025 | 10/1974 | Fowler et al. . |
| 3,905,123 | 9/1975 | Fowler et al. . |
| 3,948,277 | 4/1976 | Wochnowski et al. . |
| 4,193,116 | 3/1980 | Funk . |
| 4,255,869 | 3/1981 | Quester et al. . |
| 4,319,485 | 3/1982 | Terada et al. .......... 374/142 |
| 4,336,660 | 6/1982 | Strydom . |
| 4,462,250 | 7/1984 | Stuart .................. 73/73 |
| 4,499,111 | 2/1985 | Oetiker et al. .......... 73/73 |
| 4,503,707 | 3/1985 | Rosa et al. ............ 374/142 |

FOREIGN PATENT DOCUMENTS

| | | |
|---|---|---|
| 0034459 | 8/1981 | European Pat. Off. . |
| 0150338 | 11/1981 | Japan ................ 73/73 |
| 0169666 | 10/1982 | Japan ................ 73/73 |
| 0017350 | 2/1983 | Japan ................ 73/73 |
| 0230041 | 10/1986 | Japan ................ 73/73 |
| 0237433 | 9/1989 | Japan ................ 73/73 |
| 0302656 | 12/1990 | Japan ................ 73/73 |
| 0009809 | 1/1991 | Japan ................ 73/73 |
| 0920495 | 4/1982 | U.S.S.R. .............. 73/73 |
| 0930068 | 5/1982 | U.S.S.R. .............. 73/73 |
| 0987490 | 1/1983 | U.S.S.R. .............. 73/73 |

OTHER PUBLICATIONS

Steru, M., "Procede dielectrique pour la mesure en continu de l'humidite des materiaux solides," *Mesures Regulation Automatisme*, vol. 33, No. 1, (Jan. 1986), pp. 58-62.

"Dickey-john GAC II Grain Moisture Tester," brochure published by Dickey john, (date uknown).

"Dickey-john GAC 2000 Grain Moisture Tester", brochure published by Dickey john, (date unknown).

"Dickey-john Multi-Grain Grain Moisture Tester," brochure published by Dickey john, (date unknown).

"The MB200 Moisture Balance," brochure published by Ohaus Corporation, (1988).

"TR 400 PS Moisture Tester," brochure published by Tripette & Renaud, (date unknown).

(List continued on next page.)

*Primary Examiner*—William A. Cuchlinski, Jr.
*Assistant Examiner*—Diego F. F. Gutierrez
*Attorney, Agent, or Firm*—Willian Brinks Olds Hofer Gilson & Lione

[57] ABSTRACT

The invention relates to a moisture meter tester for granular or powdered products including a cell for the product to be analyzed and a means of indirect measurement of the moisture connected to a unit for processing the measurements, the cell being adapted to be filled with and successively emptied of the product. The moisture meter of the invention is notable in that a hygrometric sensor is arranged so as to be capable of being in contact with the air surrounding the product to be analyzed, and that the sensor is connected to the measurement processing unit in order to make corrections to the values for the apparent moisture measured by the indirect measurement means. The invention also relates to a method using such a moisture tester.

27 Claims, 4 Drawing Sheets

OTHER PUBLICATIONS

"TR 400 Auto Moisture Tester," brochure published by Tripette & Renaud, (date unknown).

"The Sinar A92 Moisture Analyser," brochure published by Sinar Technology, (date unknown).

"Steinlite SS-250 Digital Moisture Tester," brochure published by Seedburo Equipment Co., (Apr., 1979).

"Steinlite Grain and Peanut Testers," brochure published by Seedburo Equipment Co., (Jun. 1982).

"Burrows Model 700 Digital Automatic Moisture Tester," brochure, unknown publisher, (date unknown).

"Dole Digital Grain Moisture Meter—Model 500," brochure published by Eaton Corp., (date unknown).

"Dole Grain Moisture Meter—Model 400-B," brochure published by Eaton Corp., (date unknown).

"Seedburo Equipment Company," catalog published by Seedburo Equipment Company, pp. 1, 4, 5 and 7-11 (1991).

"Moisture Measurement—Grain and Seeds," Agricultural Engineers Yearbook, p. 417, (1977).

"Chapter XII. Oven Methods For Determining Moisture Content of Grain and Related Agricultural Commodities", published by U.S. Dept. of Agriculture, pp. 12.1-12.5 (Nov. 15, 1971).

"The Motomco Model 919 Moisture Meter," published by Motomco, Inc. (date unknown).

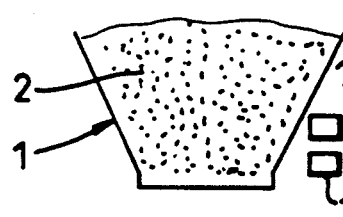
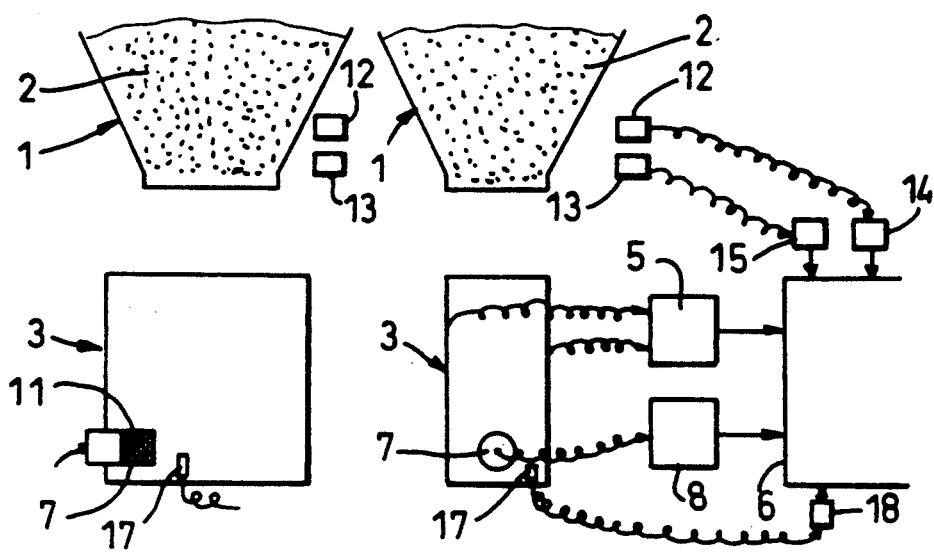
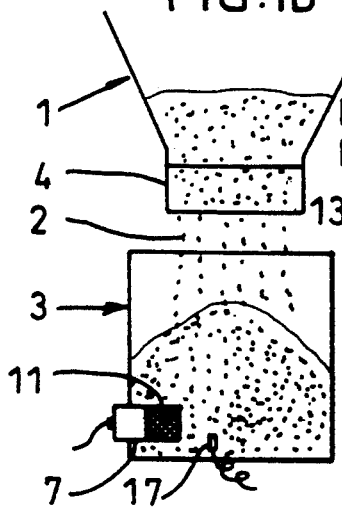
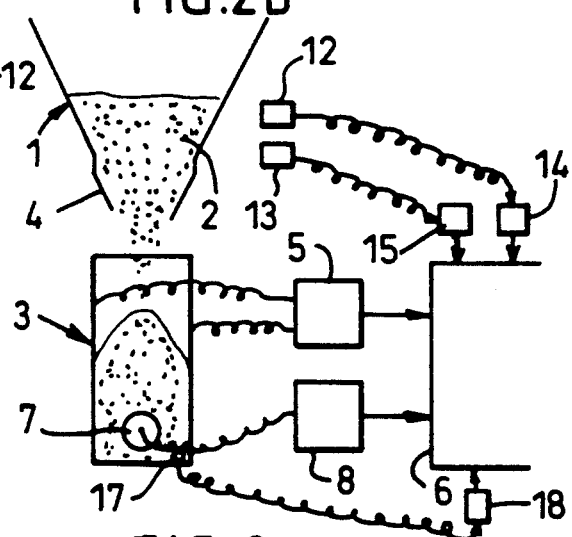
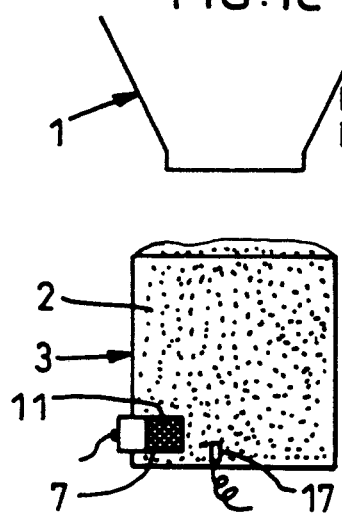
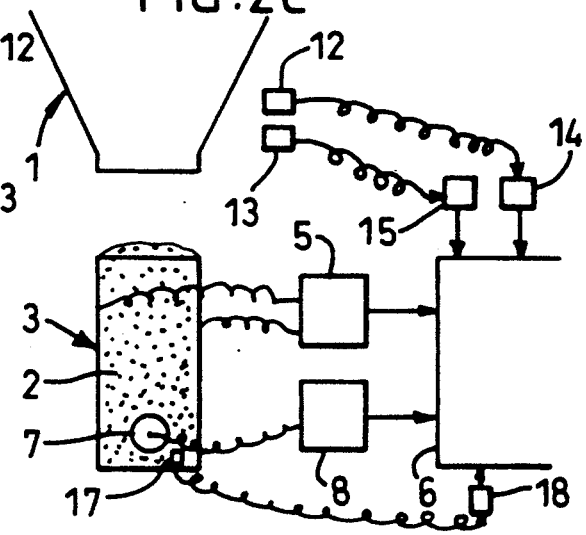

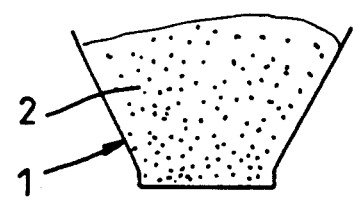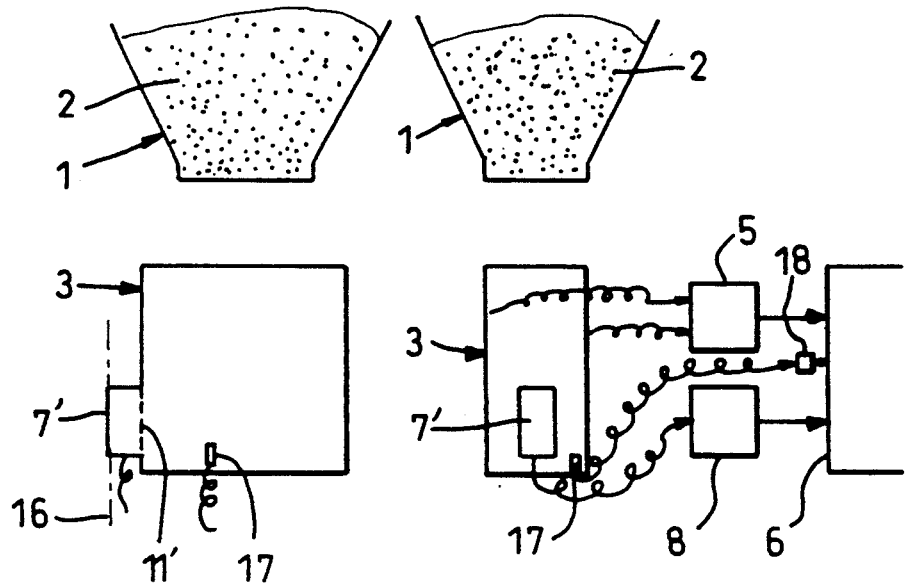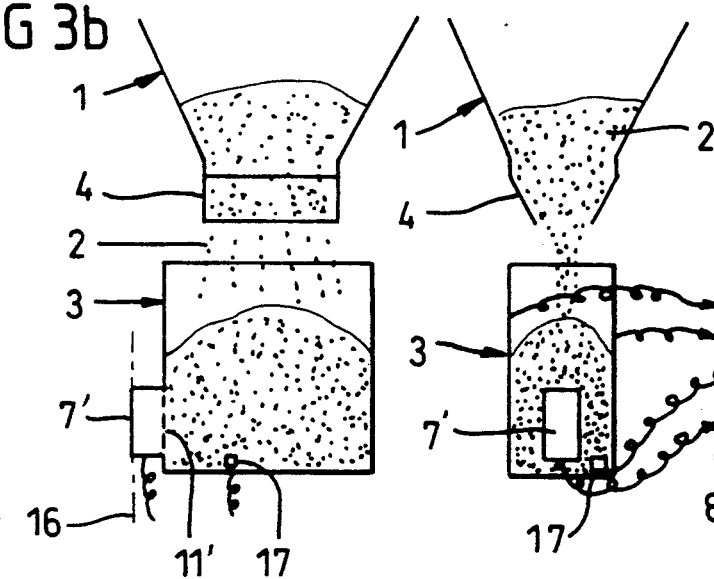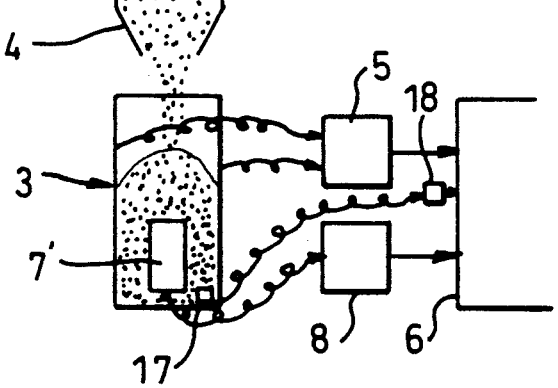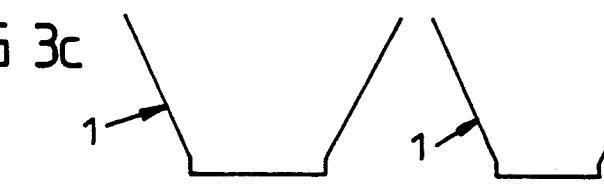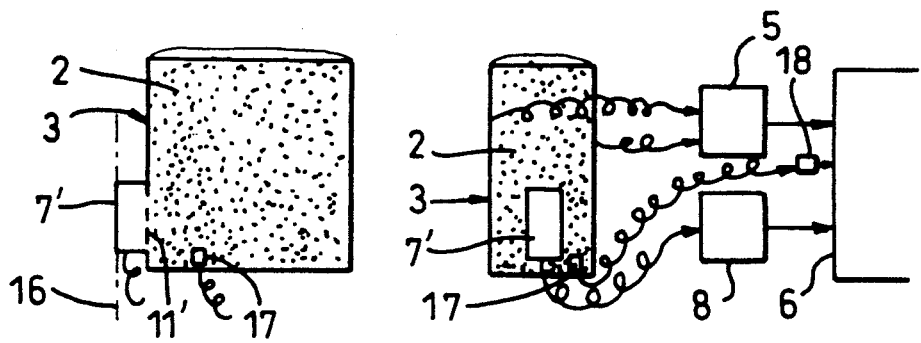

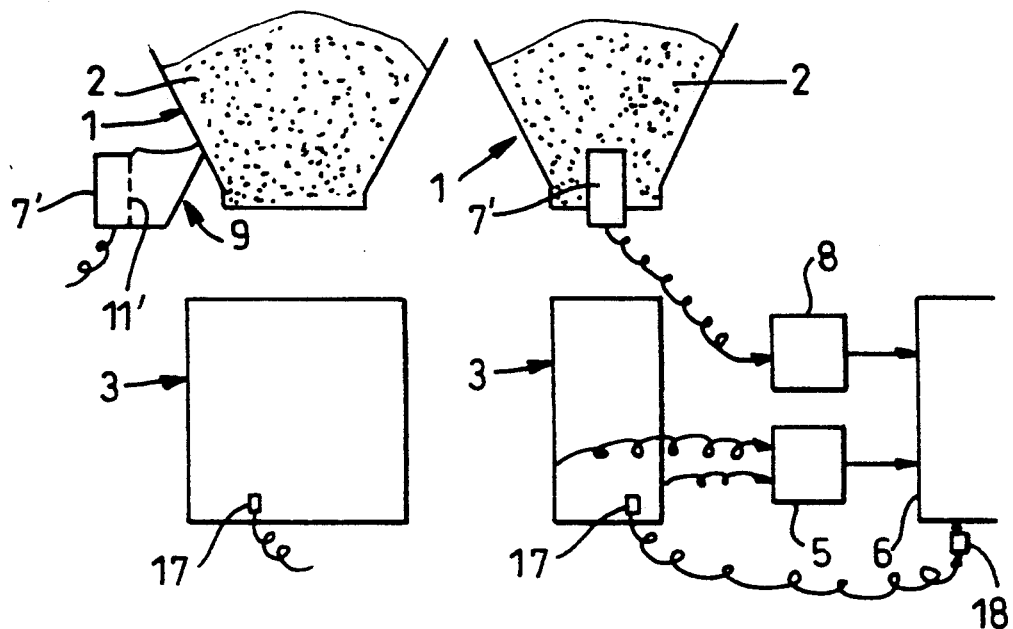
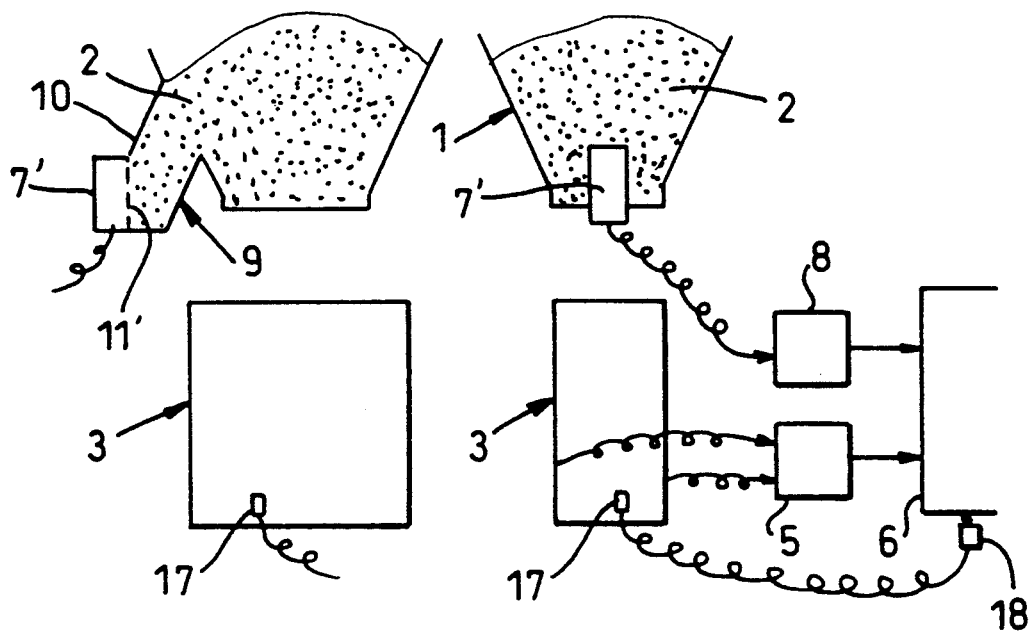

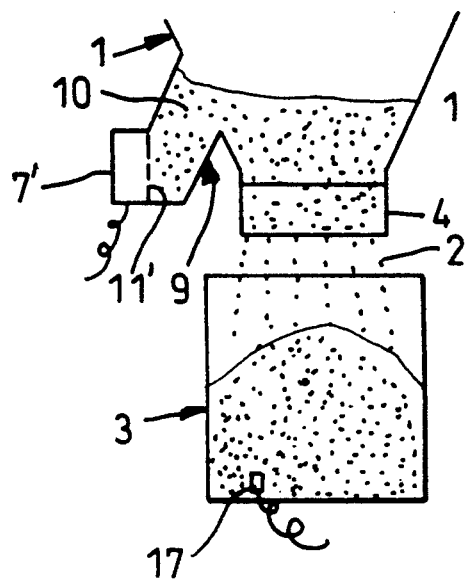
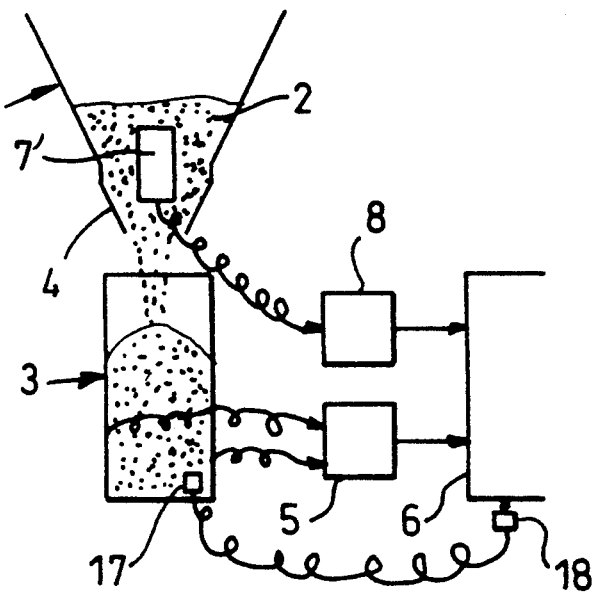
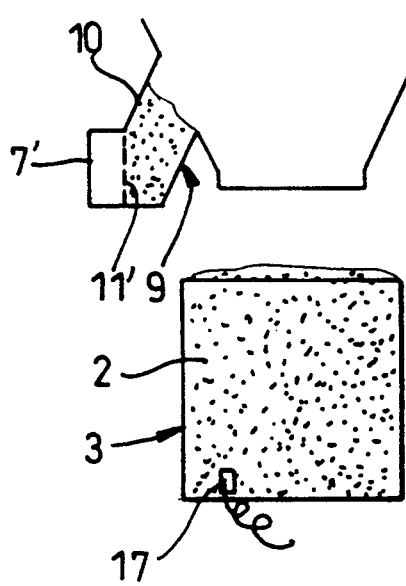
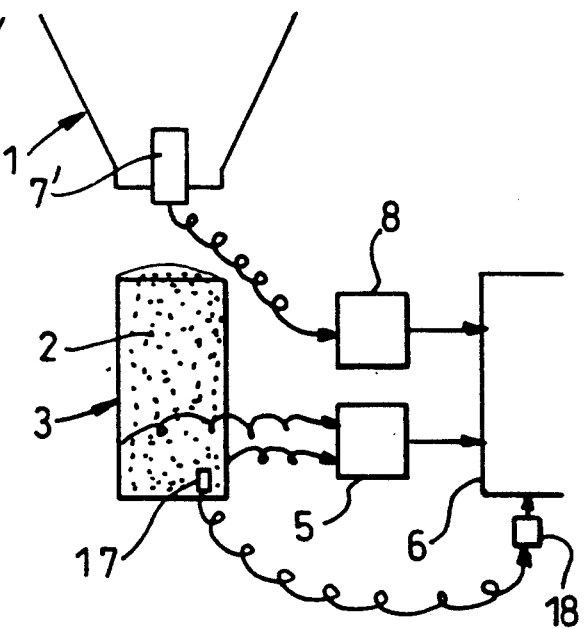

MOISTURE METER FOR GRANULAR OR POWDERED PRODUCTS, AND METHOD FOR MEASURING THE DEGREE OF MOISTURE

FIELD OF THE INVENTION

The invention relates to a moisture tester for granular or powdered products, and a method for measuring the moisture content.

BACKGROUND OF THE INVENTION

Applicants claim, under 35 U.S.C. § 119, the benefit of priority of the filing date of Jun. 13, 1991, of a French application, copy attached, Ser. No. 9107215, filed on the aforementioned date, the entire contents of which are incorporated herein by reference.

Moisture testers are currently used for cereal grains, oleaginous and proteinaceous grains or other granular or powdered products. Known moisture measurement devices generally perform indirect (for example, hyperfrequency, infrared or dielectric) measurements, and among them, the capacitive moisture testers are quite satisfactory.

Capacitive moisture testers are based on the fact that the dielectric behavior of the analyzed product varies as a function of its water content. The measurement cell is embodied constitutes at least one capacitor, and the dielectric differences between the instant when the cell is empty and the instant when the cell is filled with the product, are measured.

These dielectric measurements may be made for each product sample at a constant volume (for example, the volume of the measurement cell) or a constant weight (sample having a predetermined weight, which can be dependent on the type of product). To make these measurements, the capacitor is for instance inserted into an oscillator, as will be described in further detail hereinafter.

However, moisture testers, even of the capacitive type, have their limits, among which one in particular is the difficulty of correcting the measurement error associated with the surface moisture of the product to be analyzed. In the course of a grain harvest, for example, if one batch is exposed to rain before it is tested, the measurement done at the receiving station is erroneous, because the surface moisture (free water) is not evaluated in the same way as the internal moisture in the grain (bound water). This is because, for capacitive measurement, the bound water has a much lower dielectric constant than the free water.

Attempts to correct the capacitive measurements have therefore been made, particularly by measuring dielectric capacitance at several frequencies, or by adding a measurement of resistivity to the capacitive measurement, and so forth. These known corrective measurements have certain disadvantages. In the case of measurements of resistivity or conductibility, those measurements depend on the nature of the salts contained in the water, which can invalidate the corrective measurements.

OBJECT AND SUMMARY OF THE INVENTION

The invention relates to an improved moisture tester and method of measuring moisture which are able to correct for surface moisture of an analyzed product, and that in particular overcome the aforementioned disadvantages of making such a correction.

The invention is based on the finding that at a given temperature and pressure, moisture in the air is sensitive to the water content of the materials that are put into contact with this air. Placing a moist material in the presence of a dry gas in fact causes evaporation of the water from the material and humidification of the gas.

In a closed container in which a vacuum has been created, this evaporation continues up to a limit which depends on the temperature. At the limit the water vapor concentration is called the saturation concentration. The quantity of water vapor and its concentration directly vary as the temperature.

If the container already contains the air, the phenomena are identical, but the saturation times are longer. Consequently, at a given temperature and barometric pressure, a moist grain in the presence of dry air will have a tendency to humidify the air in its vicinity. This phenomenon will last longer, the more strongly bound the water is, and the faster the water is liberated in a major quantity at the surface of the grain.

On this basis, it has been determined that a sensor for hygrometric measurement, inserted into a batch of grain, records a variation in the water vapor concentration that is greater and faster the more moist the grain is on the surface.

These objects are attained by a moisture tester which includes a cell for the product to be analyzed and a means of indirect measurement of the moisture connected to a unit for processing the measurements, the cell being adapted to be filled with and successively emptied of the product, is notable in that a hygrometric sensor is arranged so as to be capable of being in contact with the air surrounding the product to be analyzed, and that the sensor is connected to the measurement processing unit in order to make corrections to the values for the apparent moisture measured by the indirect measurement means.

A moisture meter according to the invention thus makes it possible to achieve a method of measuring the moisture content for granular or powdered products that is remarkable in that it consists in performing, in addition to the indirect measurement of the moisture, a measurement of hygrometric values during a given period of time of the ambient air of the zone to be analyzed, on the one hand in the absence of the product and on the other in the presence of the product, to create corrective values for the apparent measured moisture value, thus by the hygrometric measurements evaluating the quantity of free water on the surface of the product.

The invention will be better understood and other features thereof will become more apparent from the ensuing detailed description, taken in conjunction with the accompanying drawings.

BRIEF DESCRIPTION OF THE DRAWINGS

FIGS. 1a–1c show a first embodiment in a schematic elevation view, in three successive phases of a measurement;

FIGS. 2a–2c correspond to FIGS. 1a–1c after a 90. rotation;

FIGS. 3a–3c and 4a–4c correspond to FIGS. 1a–1c and 2a–2c, respectively, for a second embodiment of the present invention; and FIGS. 5a–5d and 6a–6d correspond in the same manner to the above drawing figures, for a third embodiment of the present invention.

DESCRIPTION OF THE PREFERRED EMBODIMENTS

In all the drawing figures, a feed hopper 1 contains a product 2 to be analyzed, oleaginous or proteinaceous product such as cereal. The feed hopper 1 is disposed just above a measurement cell 3. Measurement cell 3 may be filled by opening a trap door 4 provided on the feed hopper 1.

A means of indirect measurement of the amount of moisture is provided. For example, a capacitive effect measurement means may be used. Such a measurement means comprises two opposed walls of the cell which form the plates or foils of a capacitor, and these two walls are also connected by way of a suitable interface 5 to an electric measurement processing unit 6.

All of the embodiments of the drawings are provided with a hygrometric sensor 7, 7' (7 in the first exemplary embodiment shown, and 7' in the others), which is also connected to the processing unit 6 by an interface 8. The processing unit 6 is designed in a function of the type of measurement used. For capacitive measurements the unit may include an oscillator, with which the frequency drift or attenuation of the fixed frequency signal can be measured when the product is introduced. A microprocessor is then provided to process the measurement information. For each type of product, calibration of the equipment makes it possible to associate the result of the measurements (variations in the frequency or amplitude) with the water content of the product. In FIGS. 2a-c, 4a-c, and 6a-c, the interface 5 is an electronic module intended for adapting and optionally converting the signal received, while the interface 8 depends on the type of hygrometric sensor shown, as will be described hereinafter.

The hygrometric sensor may be positioned at various locations. For example, in the embodiment shown in FIGS. 1a, 1b, 1c and 2a, 2b, 2c, the hygrometric sensor 7 is disposed in the lower portion of the cell 3.

In the embodiment of FIGS. 3a, 3b, 3c and 4a, 4b, 4c, the sensor 7' is arranged on the outside of the cell 3, on one of its walls, but also toward the lower portion of this cell 3. Sensor 7' may also be arranged within one of the walls of the cell, if the wall is sufficiently thick. The sensor 7' may also be at greater distances than shown as long as it remains in contact with the ambient air surrounding the product to be analyzed.

In the embodiments of 1a-c, 2a-c, 3a-c, and 4a-c, the hygrometric sensor may be disposed in the cell, being suitably isolated from the product but in communication with the ambient air of the cell.

In the embodiment of FIGS. 5a-5d and 6a-6d, the sensor 7' is arranged on an adjoining cell 9. Cell 9 is in communication with the feed hopper 1 so as to be filled by means distinct from those of the main cell, for example via a door 10 (FIGS. 5b-5d). The sensor 7' may naturally be the same type as that identified by reference numeral 7 in the first embodiment and disposed in the adjoining cell 9.

In all of the embodiments shown in the drawings sensor 7, 7' is isolated from the product to be analyzed via a filter 11, 11, or the like. The sensor 7, 7' makes a hygrometric measurement of the air in the presence of the product (and in the absence of the product, as will be explained below), and accordingly one seeks to avoid any contact of the sensitive parts of the sensor 7, 7' with the product itself by using filters.

Numerous types of hygrometric sensors exist. Certain hygrometers are provided with hairs or synthetic polymer fibers and work by stretching. Hygrometers of the capacitive type are also known that are provided with a film-type capacitor, whose dielectric value varies as a function of the degree of water vapor present. Measurement may also be based on the impedance, which varies in accordance with the water content. Hygrometric sensors called "dew point" sensors, provided with a chilled mirror or an aluminum oxide probe, are also known. However, from the standpoint of response time, dimensions, cost and interfacing, hygrometric sensors of the capacitive or impedance type are perfectly suitable.

Moreover, it is possible to add sensors for complementary measurements, such as ambient parameter, like the sensors 12 and 13 for temperature and pressure, respectively, shown by way of example in FIGS. 1a-1c and 2a-2c. The sensors 12 and 13 are connected to the processing unit 6 by interfaces 14 and 15, respectively. These sensors, which analyze the conditions of the measurement, can be disposed at numerous locations outside the cell 3. However, the pressure sensor 13 is not absolutely necessary for this type of measurement. The temperature of the grain affects the dielectric value, and a temperature sensor, such as the sensor schematically shown at 17 in the drawings, is generally provided in the cell 3 (or in the hopper 1), this sensor being connected to the processing unit 6 by an interface 18. The measurement device may optionally include a temperature sensor and/or a pressure sensor being arranged in the vicinity of the product to be analyzed but outside the measurement cells. Preferably any temperature and/or pressure measurements are performed at the same time. In this way, corrections can also be made from these complementary measurements.

The various embodiments of moisture testers described previously include numerous other means, not shown, to assure the various operational phases, in particular filling and evacuation of the cells and hopper. For example the cell 3 and the adjoining cell 9 are provided with suitable means (not shown) for their evacuation, such as doors, for example of the same type as the door 4 of the hopper 1.

With the embodiments of FIGS. 1a-1c, 2a-2c on the one hand, and 3a-3c, 4a-4c on the other, one is able to perform a method of measuring the moisture content of a product. The first step of the method comprises a hygrometric measurement in the absence of the product performed by the sensor 7, 7' for a given period of time. Next, a hygrometry measurement is made in the cell 3 in the presence of the product, as well as an indirect measurement of the moisture content (for example by capacitive effect) when the cell 3 is filled.

The position of the sensor 7, 7' at the bottom of the cell 3 makes it possible to increase the length of time available for performing the hygrometric measurement in the presence of the product, without also increasing the total duration of the method. The above mentioned measurements make it possible to make corrections which there has already been some mention, while the sensors 12 and 13 make measurements of the surroundings during this time.

Regarding the embodiment of FIGS. 5a-5d and 6a-6d, the method is substantially the same, except in the step where a hygrometry measurement is taken in the presence of the product, the adjoining cell 9 is first filled before the main cell, so as to have additional time available for the hygrometric measurements in the presence of the product. Other steps of the method are apparent upon viewing the figures. For example, FIGS. 5a, 6a corresponding to measurements in a vacuum and FIGS. 5c and 6c corresponding to filling (optionally while the hygrometry measurements are still being made). FIGS. 5d and 6d correspond to the effective measurements of moisture (after filling). However, it is clear that with an embodiment in accordance with FIGS. 5a–5d and 6a–6d, it is possible to have a particularly long period of time available for hygrometric measurement in the presence of the product, since the cell 9 can be filled (via the door 10) very quickly.

Next, the cell 3 is evacuated, as already noted, as is the adjoining cell 9. The adjoining cell may be evacuated simultaneously with the cell 3, for example, or just before it as long as the evacuation of the adjoining cell takes place no later than simultaneously with that of the main cell.

As has already been noted, the variations in hygrometry associated with the surface moisture are rapid, and the various measurements made during a given period of time thus make it possible to establish a family of variation curves, such that in one embodiment of the invention, the corrective values may be established by extrapolation from the curve of the hygrometric values measured during the given period of time.

One of ordinary skill would understand that the hygrometric curves are obtained by measuring and plotting the humidity, H(t), of the air surrounding the product to be analyzed as a function of time. The first point of the curve H(O) is at time=t=0 s and corresponds to when there is no product present. H(t>0) corresponds to the humidity of the air surrounding the product when the product is present in the cell. The humidity variation due to surface moisture from the product is $\Delta H = H(t) - H(O)$. Thus, one takes a plurality of measurements of H(t) and subtracts the humidity when no product is present. As mentioned before, H(t) increases with time but levels off to a maximum value upon saturation.

The different $\Delta H$ represents the humidity caused by the product. The $\Delta H$ curve also increases with time and levels off to a maximum value, $\Delta H(max)$, at the saturation point. From the $\Delta H$ curve one can extrapolate so as to determine the value of $\Delta H$ (max). One of ordinary skill would recognize that the value of $\Delta H(max)$ would be dependent on such parameters as H(t), H(O), t, the type of grain, the pressure, the temperature when no product is present, and the temperature when the product is present. Furthermore, the values for $\Delta H(max)$ for various grains, temperatures, and pressures can be stored in a memory.

Once the $\Delta H$ curve is determined, then it is possible to determine a corrected moisture content, M (corrected), which takes into account the water content of the grain. Since the water content of the grain is directly related to the value of $\Delta H(max)$, one of ordinary skill would expect that M (corrected) would be a function of (1) the apparent moisture content, M(apparent), as measured by the indirect measurement device; (2) $\Delta H(max)$; and (3) the type of grain measured. Thus, one of ordinary skill would then construct a family of curves for a particular temperature, pressure, grain, and thus a particular $\Delta H(max)$, so that by measuring M (apparent) one could determine the true moisture content M (corrected).

The invention may be embodied in other forms than those specifically disclosed herein without departing from its spirit or essential characteristics. For example, the invention may employ means for leveling off the cell or means for filling and evacuation. An example of a leveling system for a cell is Applicant's own pending U.S. application titled "Measurement Cell For Granular Or Powdered Products" and filed simultaneously with the present application and having a Ser. No. 07/897,270. The described embodiments are to be considered in all respects only as illustrative and not restrictive, and the scope of the invention is commensurate with the appended claims rather than the foregoing description.

I claim:

1. A moisture tester for analyzing granular or powdered product, comprising:
   a measurement cell for the product to be analyzed, wherein said cell is filled with and successively emptied of said product;
   a means of indirect measurement of the moisture of the product;
   a measurement processing unit for processing the measurement from said means for indirect measurement; and
   a hygrometric sensor arranged so as to be in contact with the air surrounding said product to be analyzed and wherein said sensor is connected to the measurement processing unit in order to make corrections to the values for the apparent moisture measured by said indirect measurement means.

2. The moisture tester of claim 1, wherein the hygrometric sensor is disposed int he cell such that the sensor is suitably isolated from the product but in communication with the ambient air of the cell.

3. The moisture tester of claim 2, wherein the hygrometric sensor is disposed toward a lower portion of the cell.

4. The moisture tester of claim 1, wherein the hygrometric sensor is disposed in a wall of the cell such that the sensor is suitably isolated from the product but in communication with the ambient air of the cell.

5. The moisture tester of claim 4, wherein the hygrometric sensor is disposed toward a lower portion of the cell.

6. The moisture tester of claim 1, wherein the hygrometric sensor is disposed on the outside of the cell but in the vicinity of one of its walls such that the sensor is suitably isolated from the product but in communication with the ambient air of the cell.

7. The moisture tester of claim 6, wherein the hygrometric sensor is disposed toward a lower portion of the cell.

8. The moisture tester of claim 1, wherein the hygrometric sensor is disposed toward a lower portion of the cell.

9. The moisture tester of claim 1, comprising:
   a feed hopper for the product arranged above the measurement cell;
   an adjoining cell which is in communication with said feed hopper so as to be filled with the product to be analyzed and wherein the hygrometric sensor is disposed in or on said adjoining cell and the sensor is suitably isolated from the product when the product fills the adjoining cell but communicating with the ambient air of said adjoining cell;
   said adjoining cell comprising filling means as well as evacuation means.

10. The moisture tester of claim 1, comprising a temperature sensor arranged in the cell.

11. The moisture tester of claim 10, comprising a second temperature sensor arranged in the vicinity of the product and outside the measurement cell.

12. The moisture tester of claim 11, comprising a pressure sensor arranged in the vicinity of the product and outside the measurement cell.

13. The moisture tester of claim 10, comprising a pressure sensor arranged in the vicinity of the product and outside the measurement cell.

14. The moisture tester of claim 1, comprising a temperature sensor arranged in a feed hopper.

15. The moisture tester of claim 14, comprising a second temperature sensor arranged in the vicinity of the product and outside the measurement cell.

16. The moisture tester of claim 15, comprising a pressure sensor arranged in the vicinity of the product and outside the measurement cell.

17. The moisture tester of claim 14, comprising a pressure sensor arranged in the vicinity of the product and outside the measurement cell.

18. A method of measuring the moisture content for granular or powdered products by means of a moisture tester comprising the steps of:
providing an empty main cell;
measuring, during a given period of time, a hygrometric value of the ambient air of a zone of the empty main cell;
placing said granular or powdered product into said empty main cell;
measuring during a given period of time hygrometric values of the ambient air of a zone of the main cell containing said granular or powdered product in said main cell;
indirectly determining the apparent moisture content of the granular or powdered product contained by said main cell;
determining corrective values for the apparent measured moisture value based upon the hygrometric values measured with the empty main cell and the main cell containing said granular or powdered product; and
correcting said apparent moisture content based upon said corrective values for the apparent measured moisture value.

19. The method of claim 18, comprising the step of taking a temperature measurement at the same time as the hygrometric measurement.

20. The method of claim 19, comprising the step of taking a pressure measurement at the same time as the hygrometric measurement.

21. The method of claim 19, comprising the step of determining corrective values comprises extrapolating from a curve of the hygrometric values measured with the empty main cell and the main cell containing said granular or powdered product.

22. The method of claim 21, comprising the step of:
providing an adjoining cell which adjoins said main cell;
filling the adjoining cell with a granular or powdered product before said granular or powdered product is place in the empty main cell, so as to have additional time available for the hygrometric measurements in the presence of the product, while the evacuation of the adjoining cell takes place no later than simultaneously with that of the main cell.

23. The method of claim 19, comprising the step of:
providing an adjoining cell which adjoins said main cell;
filling the adjoining cell with a granular or powdered product before said granular or powdered product is place in the empty main cell, so as to have additional time available for the hygrometric measurements in the presence of the product, while the evacuation of the adjoining cell takes place no later than simultaneously with that of the main cell.

24. The method of claim 18, comprising the step of taking a pressure measurement at the same time as the hygrometric measurement.

25. The method of claim 18, wherein the step of determining corrective values comprises extrapolating from a curve of the hygrometric values measured with the empty main cell and the main cell containing said granular or powdered product.

26. The method of claim 25, comprising the step of:
providing an adjoining cell which adjoins said main cell;
filling the adjoining cell with a granular or powdered product before said granular or powdered product is place in the empty main cell, so as to have additional time available for the hygrometric measurements in the presence of the product, while the evacuation of the adjoining cell takes place no later than simultaneously with that of the main cell.

27. The method of claim 18, comprising the step of:
providing an adjoining cell which adjoins said main cell;
filling the adjoining cell with a granular or powdered product before said granular or powdered product is place in the empty main cell, so as to have additional time available for the hygrometric measurements in the presence of the product, while the evacuation of the adjoining cell takes place no later than simultaneously with that of the main cell.

* * * * *

UNITED STATES PATENT AND TRADEMARK OFFICE
CERTIFICATE OF CORRECTION

PATENT NO. : 5,253,512
DATED : October 19, 1993
INVENTOR(S) : Dominique Le Gigan It is certified that error appears in the above-indentified patent and that said Letters Patent is hereby corrected as shown below:

In the Abstract, line 1, delete "meter".

In the Abstract, line 7, delete "meter" and substitute therefor --tester--.

In column 1, line 26, delete "is" and substitute therefor --as--.

In column 2, line 38, delete "meter" and substitute therefor --tester--.

In column 2, line 61, delete "90" and substitute therefor --90°--.

In column 3, line 2 delete "analyzed ," and substitute therefor --analyzed, such as cereal,--.

In column 3, line 3, delete "product such as cereal" and substitute therefor --products--.

UNITED STATES PATENT AND TRADEMARK OFFICE
CERTIFICATE OF CORRECTION

PATENT NO. : 5,253,512
DATED : October 19, 1993
INVENTOR(S) : Dominique Le Gigan It is certified that error appears in the above-indentified patent and that said Letters Patent is hereby corrected as shown below:

In column 3, line 63, delete the second occurrence of "11" and substitute therefor -- 11' --.

In column 4, line 16, after "parameter" insert --sensors--.

In column 4, line 59, delete "above mentioned" and substitute therefor --above-mentioned--.

In column 4, line 60, after "corrections" insert --, of--.

In column 5, line 32, delete "(O)" and substitute therefor --(0)--.

In column 5, line 37, delete "(O) and substitute therefor --(0)--.

In column 5, line 42, delete "different" and substitute therefor --difference--.

In column 5, line 48, delete "(O)" and substitute therefor --(0)--.

UNITED STATES PATENT AND TRADEMARK OFFICE
CERTIFICATE OF CORRECTION

PATENT NO. : 5,253,512
DATED : October 19, 1993
INVENTOR(S) : Dominique Le Gigan It is certified that error appears in the above-indentified patent and that said Letters Patent is hereby corrected as shown below:

In Col. 6, line 33, delete "int he" and substitute therefor --in the--.

In Col. 8, line 1, delete "comprising" and substitute therfor --wherein--.

In Col. 8, line 11, delete "place" and substitute therefor --placed--.

In Col. 8, line 21, delete "place" and substitute therefor --placed--.

In Col. 8, line 39, delete "place" and substitute therefor --placed--.

In Col. 8, line 49, delete "place" and substitute therefor --placed--.

Signed and Sealed this

Fifteenth Day of November, 1994

Attest:

BRUCE LEHMAN

Attesting Officer

Commissioner of Patents and Trademarks